ns of the Periodic Table and in the presence of an ether as reaction medium at a temperature of about between 1 to 300 bar and in a temperature range of about 0° to 200° C. According to the disclosed invention, the magnesium hydride is activated by grinding to a particle size of ≦10 μm and the method is carried out in the absence of complex catalysts. The grinding of the magnesium hydride takes place prior to the reaction with the olefin, but may also be conducted during the reaction.

United States Patent [19]
Klein et al.

[11] Patent Number: 5,221,499
[45] Date of Patent: Jun. 22, 1993

[54] METHOD FOR THE PREPARATION OF DIALKYLMAGNESIUM COMPOUNDS BY THE REACTION OF MAGNESIUM HYDRIDE WITH AN OLEFIN

[75] Inventors: Klaus-Dieter Klein, Muelheim a.d. Ruhr; Wilfried Knott; Goetz Koerner, both of Essen, all of Fed. Rep. of Germany

[73] Assignee: Th. Goldschmidt AG, Essen, Fed. Rep. of Germany

[21] Appl. No.: 869,260

[22] Filed: Apr. 15, 1992

[30] Foreign Application Priority Data

May 18, 1991 [DE] Fed. Rep. of Germany ....... 4116382

[51] Int. Cl.$^5$ ............................................. C07F 3/02
[52] U.S. Cl. ............................................. 260/665 R
[58] Field of Search ................................... 260/665 R

[56] References Cited

U.S. PATENT DOCUMENTS 4,615,843 10/1986 Fannin et al. ................ 260/665 R

FOREIGN PATENT DOCUMENTS 0014983 9/1980 European Pat. Off. .
0177749 4/1986 European Pat. Off. .
0814708 6/1959 United Kingdom .

Primary Examiner—Paul J. Killos
Assistant Examiner—Porfirio Nazario
Attorney, Agent, or Firm—Anderson Kill Olick & Oshinsky

[57] ABSTRACT

A method for the preparation of dialkylmagnesium compounds is disclosed, wherein magnesium hydride is reacted with an olefin in the presence of a halide of sub-groups IV to VIII of the Periodic Table and in the presence of an ether as reaction medium at a temperature of about between 1 to 300 bar and in a temperature range of about 0° to 200° C. According to the disclosed invention, the magnesium hydride is activated by grinding to a particle size of ≦10 μm and the method is carried out in the absence of complex catalysts. The grinding of the magnesium hydride takes place prior to the reaction with the olefin, but may also be conducted during the reaction.

4 Claims, No Drawings

METHOD FOR THE PREPARATION OF DIALKYLMAGNESIUM COMPOUNDS BY THE REACTION OF MAGNESIUM HYDRIDE WITH AN OLEFIN

FIELD OF THE INVENTION

The invention generally relates to dialkylmagnesium compounds and is particularly directed to a method for the preparation of dialkylmagnesium compounds by the reaction of magnesium hydride with an olefin in the presence of halides of sub-groups IV to the VIII of the Periodic Table, wherein an ether is used as reaction medium and the reaction is carried out at a pressure of about between 1 to 300 bar and in a temperature range of about between 0° to 200° C.

BACKGROUND INFORMATION AND PRIOR ART

The closest prior art known to the applicants is European Patent No. 0 014 983. This European patent is directed to a method for the preparation of dialkylmagnesium compounds $R_2Mg$, wherein R is alkyl, by the reaction of magnesium hydride $MgH_2$ or magnesium and hydrogen with an olefin in the presence of a catalyst. The gist of the process is the nature of the catalyst. Thus, the catalyst may either be (a) magnesium organic compounds together with halides of a transition metal of sub-groups IV to VIII of the Periodic System, or (b) magnesium hydride together with halides of sub-groups IV to VIII of the Periodic System. The magnesium hydride or catalyst (b), in turn, has been prepared from magnesium and hydrogen (1 to 300 bar) in the presence of a polycyclic aromatic compound and, optionally, a tertiary amine as activators at temperatures of 0° to 200° C.

Pursuant to this prior art disclosure, the reaction is carried out preferably in the presence of a solvent, tetrahydrofuran being the preferred solvent. The patent teaches that the preferred reaction conditions are pressures of 1 to 300 bar and temperatures of 0° to 200° C.

The preparation of the catalyst as identified above is disclosed and described in the examples of the European patent 0 014 983. Corresponding to these examples, magnesium powder (50 mesh) is first suspended in tetrahydrofuran. Ethyl bromide is added to the suspension and after stirring for half an hour, anthracen is added. The mixture is continually agitated until formation of the magnesium anthracen has taken place. Subsequently, the halide, e.g., chloride, of sub-groups IV through VIII of the Periodic System or Table is added to the mixture. Examples of such chlorides are $CrCl_3$, $TiCl_4$, $NiCl_2$, $VCl_4$, $ZrCl_4$ and $HfCl_4$. After further stirring, the desired colored catalyst solution is formed, the color being dependent on the nature of the halide.

Pursuant to the teaching of this European Patent 0 014 983, this catalyst solution is admixed with magnesium hydride. This results in a suspension and the olefin is now added to this suspension. The addition reaction of the olefin takes place in a temperature range of 0° to 200° C. and at a pressure of 1 to 300 bar.

OBJECTS OF THE INVENTION

It is a primary object of the invention to prepare dialkylmagnesium compounds by reaction of magnesium hydride with an olefin in a simpler and more economic manner as has been possible with prior art methods.

In particular, it is an object to avoid complex catalysts and the use of polycyclic aromatic compounds.

SUMMARY OF THE INVENTION

Pursuant to the method of the invention, dialkylmagnesium compounds are produced in the manner described above, the magnesium hydride, however, having been activated prior to the reaction with the olefin by grinding to a particle size of $\leq 10$ μm. The method can then be carried out entirely without the addition of complex catalysts. In a modified form of the inventive method, the grinding is also additionally performed during the reaction with the olefin.

It will be appreciated that it was surprising that the grinding of the magnesium hydride to a particle size of $\leq 10$ μ, and in particular $\leq 1$ μ, causes such activation of the magnesium hydride that the addition reaction of the olefin in the presence of halides of the sub-groups IV to VIII is accomplished without requiring further catalysts and that the product is obtained in high yields.

In order to carry out the inventive procedure, the magnesium hydride is suspended in an ether, preferably tetrahydrofuran or deglyme. Additional examples of suitable ethers are dioxane and diethyl ether. The suspension thus obtained is charged to a grinding apparatus. Suitable grinding arrangements or devices are vibrating or oscillating disc mills, mills of the attrition type, ball mills of the annular gap agitation type, Wheeler mills, Jet-O-Mizers, Eagle type mills and fluidized bed jet mills. Also, so-called bead mills of the type Dynomill or Supermill are advantageously employed. However, the nature of the mill is not critical as long as the desired result is obtained. The grinding is performed for a period until the particle size of the magnesium hydride is $\leq 10$ μ. Preferably, a particle size in the range of about 1.5 to 1μ should be the end result of the grinding.

The halides of the sub-groups IV to VIII of the Periodic System are now added to this suspension in the usual amounts. The quotient formed by the amount of magnesium and transition metal halide should have a value of 10,000 to 1. As transition metal halides, the halides mentioned in European Patent 0 014 983 can suitably be used as, for example, $CrCl_3$, $TiCl_4$, $NiCl_2$, $VCl_4$, and $HfCl_3$.

During the reaction of the magnesium hydride with the olefin, the magnesium hydride particles of the smallest diameter are preferentially reacted in the beginning phases of the reaction. Accordingly, it is oftentimes advantageous to continue the grinding of the magnesium hydride, and thus this activation, also during the reaction with the olefin, so that very fine particles of the magnesium hydride are continuously available for reaction.

As magnesium hydride, it is preferred to use a storage magnesium hydride which from the very outset has a relatively small particle size and is capable of being poured. Such storage magnesium hydride may be produced corresponding to German patent application No. P 40 27 976.6.

As far as the olefin is concerned, preferably α-olefins of the general formula $CH_2=CHR$, wherein R stands for hydrogen, alkyl or cycloalkyl are used. The group R generally has 1 to 10 carbon atoms.

Examples of suitable alkyl groups of the indicated kind are ethyl, propyl, butyl, pentyl, hexyl, octyl, nonyl and decyl.

The addition reaction is, as a rule, concluded within a time frame of about 4 to 48 hours.

In a preferred embodiment of the inventive procedure, the method is carried out in the presence of catalytic amounts of an aluminum trialkyl. As alkyl groups, particularly those come into consideration which have 1 to 4 carbon atoms, preferably ethyl groups. The term "catalytic amount" as used hereinabove means amounts of about 1 to 5 mole % calculated on $MgH_2$. The addition of this non-complex catalyst results in an increase in the yield of dialkylmagnesium compound.

The invention will now be described by several examples, it being understood that these examples are given by way of illustration and not by way of limitation, and that many changes may be effected without affecting in any way the scope and spirit of the invention as recited in the claims.

EXAMPLE 1

This example was carried out with storage magnesium hydride $MgH_2$ which had been produced from magnesium and hydrogen and which had an average particle size of 0.054 mm. This magnesium hydride was ground for 20 minutes in an oscillating disk mill under an inert gas atmosphere. 11.26 gram (0.402 mole) of this preactivated magnesium hydride was charged into a laboratory ball mill and, in the indicated sequence, 366 ml of THF, 2.8 gram (0.012 mole) of $ZrCl_4$ and 90.2 gram (0.804 mole) of 1-octene were added to the magnesium hydride in the mill. The reaction batch was constantly ground and, during the grinding, was heated for 15 hours at reflux temperature. By means of a syringe, a sample was removed from the mill and was centrifuged for 1 hour at 4000 RPM under an inert gas atmosphere. An aliquot portion of the clear, supernatant liquid was removed and hydrolyzed, whereupon the amount of magnesium was determined complexometrically while the content of the octane was determined gas-chromatographically. The yield was 34% calculated on the amount of $MgH_2$ initially used.

EXAMPLE 2

This experiment was carried out in a laboratory ball mill with 28.0 g (1.0 mole) of 94% storage magnesium hydride $MgH_2$ of an average particle size of 0.054 mm in 475 ml of THF. The mixture in the ball mill was ground for 10 hours. 2.33 g (0.0094 mole) of $ZrCl_4$ and 210.8 g (2.50 mole) of 1-hexene were added one after the other, and the reaction batch under constant grinding for 24 hours was heated to reflux temperature.

The sample was removed via syringe and was centrifuged for 1 hour at 4000 RPM under an inert gas atmosphere. An aliquot portion of the clear supernatant liquid was removed and hydrolyzed. Subsequently, the magnesium content was determined complexometrically while the content of hexene was determined gas-chromatographically. The yield was 30% calculated on the $MgH_2$ initially used.

EXAMPLE 3

This experiment was carried out in a 300 ml laboratory autoclave with magnetic stirrer. 4.3 g (0.152 mol) of magnesium hydride $MgH_2$ were charged into the autoclave. The magnesium hydride was obtained by grinding of storage hydride with an average particle size of 0.054 mm in an oscillating disc mill for 20 minutes under an inert gas atmosphere. 1.1 g (0.0047 mol) $ZrCl_4$ and 158.4 g of THF were added. The autoclave was then closed and was charged with 30 bar ethylene $C_2H_4$. The reaction batch is heated under stirring for 18 hours to 75° C. After completed reaction, the autoclave is permitted to cool down and the pressure is released slowly. The dark brown colored reaction solution is transferred into an argon-filled vessel. In addition to unreacted $MgH_2$, a small amount of solid polyethylene (5.1 g) remains in the autoclave.

The complexometric and acidimetric analysis of the reaction solution indicates a yield of 24% magnesium diethyl calculated on $MgH_2$.

EXAMPLE 4

A solution of 49 g (77 ml, 0.7 mol) of 1-pentane in 250 ml absolute tetrahydrofuran is charged to 13.8 g (95%, 0.5 mol) of magnesium hydride under protected gas vapor. The magnesium hydride had been admixed with 3.9 g (0.015 mol) $ZrCl_4$. The mixture was ground for 24 hours under reflux temperature. The inner temperature of 55° C. was not exceeded during the entire period.

The magnesium hydride used was preground in an oscillating disc mill and was immediately used for the indicated purpose.

The yield of dipentylmagnesium was determined complexometrically and amounted to 25%.

EXAMPLE 5

This experiment was carried out in a laboratory ball mill. 5.8 g (0.2 mol) of 91% storage magnesium hydride $MgH_2$ which, corresponding to Example 3, had been ground in an oscillating disc mill for 20 minutes under inert gas atmosphere, were charged into the mill. 284 ml of THF were present in the ball mill. 0.69 g (0.006 mol) of $(C_2H_5)_3Al$, 1.7 g (0.006 mol) $ZrCl_4$ and 44.9 g (0.4 mol) of 1-octene were added one after the other to the mixture in the mill. The reaction batch was constantly ground and heated to the reflux temperature. A sample was removed with a syringe and was centrifuged for 1 hour at 4000 rpm under inert gas atmosphere. An aliquot portion of the clear supernatant liquid was removed and was hydrolyzed. Subsequently, the magnesium content was determined complexometrically and the contents of octane was determined gas chromatographically. The yield was 84% (calculated on the amount of $MgH_2$).

What is claimed is:

1. In a method for the preparation of dialkylmagnesium compounds by the reaction of magnesium hydride with an olefin in the presence of a halide of subgroups IV to VIII of the Periodic Table and of an ether as reaction medium and wherein the method is carried out at a pressure of about between 1 to 300 bar and at a temperature of about between 0° to 200° C., the improvement which comprises that the magnesium hydride, prior to the reaction with the olefin, has been activated by grinding to a particle size of $\leq 10$ μm and that the procedure is carried out in the absence of a complex catalyst.

2. The improvement of claim 1, wherein the grinding is also performed during the reaction with the olefin.

3. The improvement of claims 1 or 2, wherein the method is carried out in the presence of catalytic amounts of aluminumtrialkyl.

4. The improvement as claimed in claim 3, wherein the aluminumtrialkyl is aluminumtriethyl.

* * * * *